United States Patent
Furst

(10) Patent No.: US 6,206,916 B1
(45) Date of Patent: Mar. 27, 2001

(54) COATED INTRALUMINAL GRAFT

(76) Inventor: Joseph G. Furst, 1530 Richmond Rd., Lyndhurst, OH (US) 44124

( * ) Notice: Subject to any disclaimer, the term of this patent is extended or adjusted under 35 U.S.C. 154(b) by 0 days.

(21) Appl. No.: 09/363,052

(22) Filed: Jul. 29, 1999

Related U.S. Application Data

(63) Continuation-in-part of application No. 09/273,736, filed on Mar. 22, 1999.
(60) Provisional application No. 60/094,250, filed on Jul. 27, 1998, and provisional application No. 60/081,824, filed on Apr. 15, 1998.

(51) Int. Cl.$^7$ ........................................... A61F 2/06
(52) U.S. Cl. ........................................ 623/1.46; 623/1.44
(58) Field of Search ..................... 623/1.11, 1.16, 623/1.15, 1.27, 1.39, 1.46, 1.44

(56) References Cited

U.S. PATENT DOCUMENTS

| 5,755,781 | 5/1998 | Jayaraman . | |
|---|---|---|---|
| 5,824,045 | * 10/1998 | Alt | 623/1.46 |
| 5,879,370 | 3/1999 | Fischell et al. . | |
| 5,911,732 | 6/1999 | Hojeibane . | |
| 5,964,798 | 10/1999 | Imran . | |
| 6,099,561 | * 8/2000 | Alt | 623/1.44 |

* cited by examiner

Primary Examiner—Kevin Truong
(74) Attorney, Agent, or Firm—Vickers, Daniels & Young

(57) ABSTRACT

An expandable intraluminal graft for use within a body cavity having a tubular shaped member with two ends and a wall surface disposed between the ends. The tubular shaped member has a first diameter to permit intraluminal delivery of the member into a body cavity, and a second expanded diameter. Coated on the surface of the tubular shaped member is a substance that inhibits and/or reduces restenosis, vascular narrowing and/or in-stent restenosis.

45 Claims, 6 Drawing Sheets

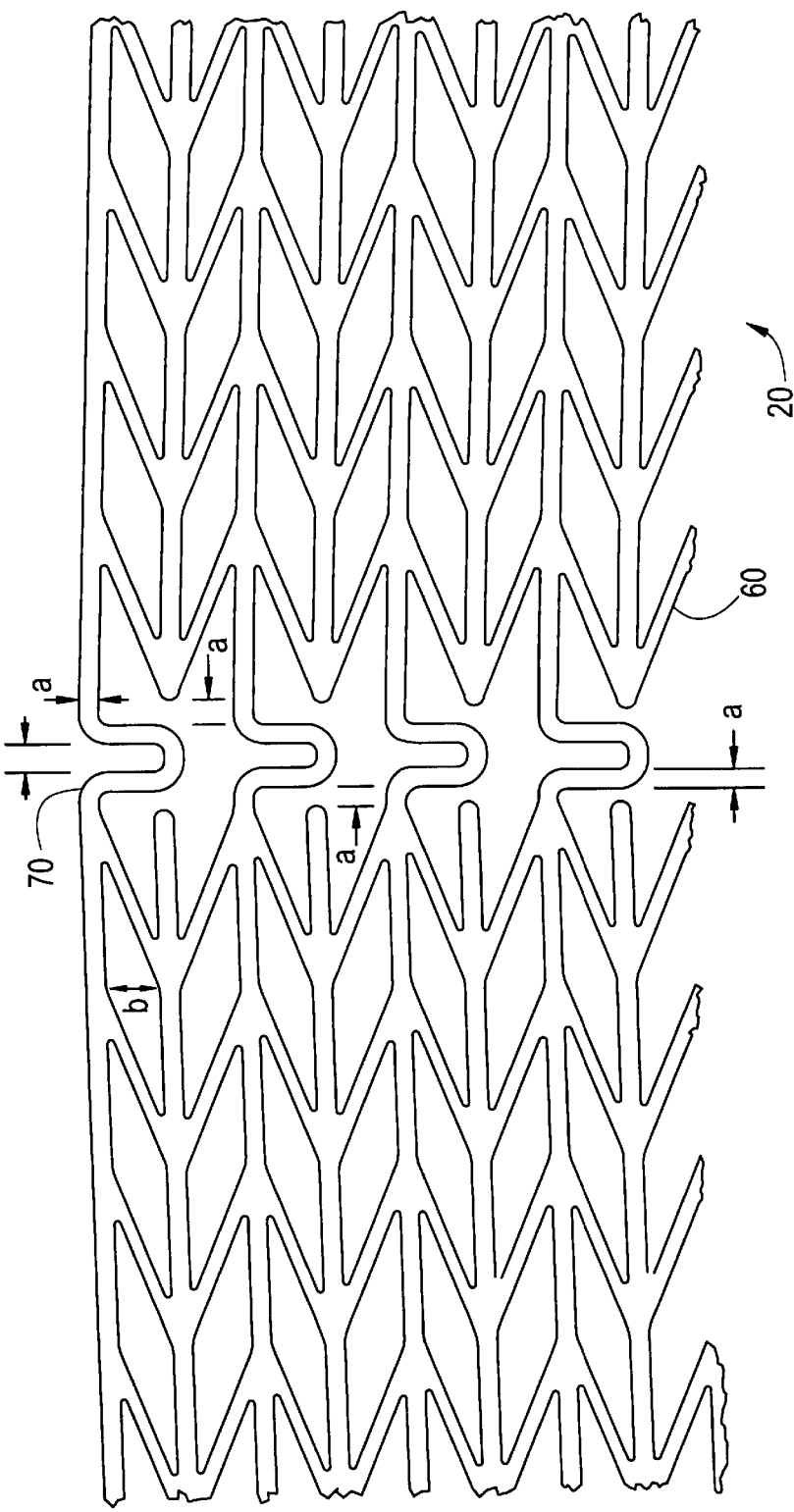
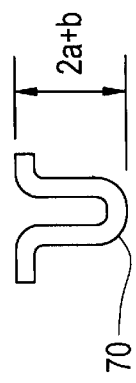

FIG. 7
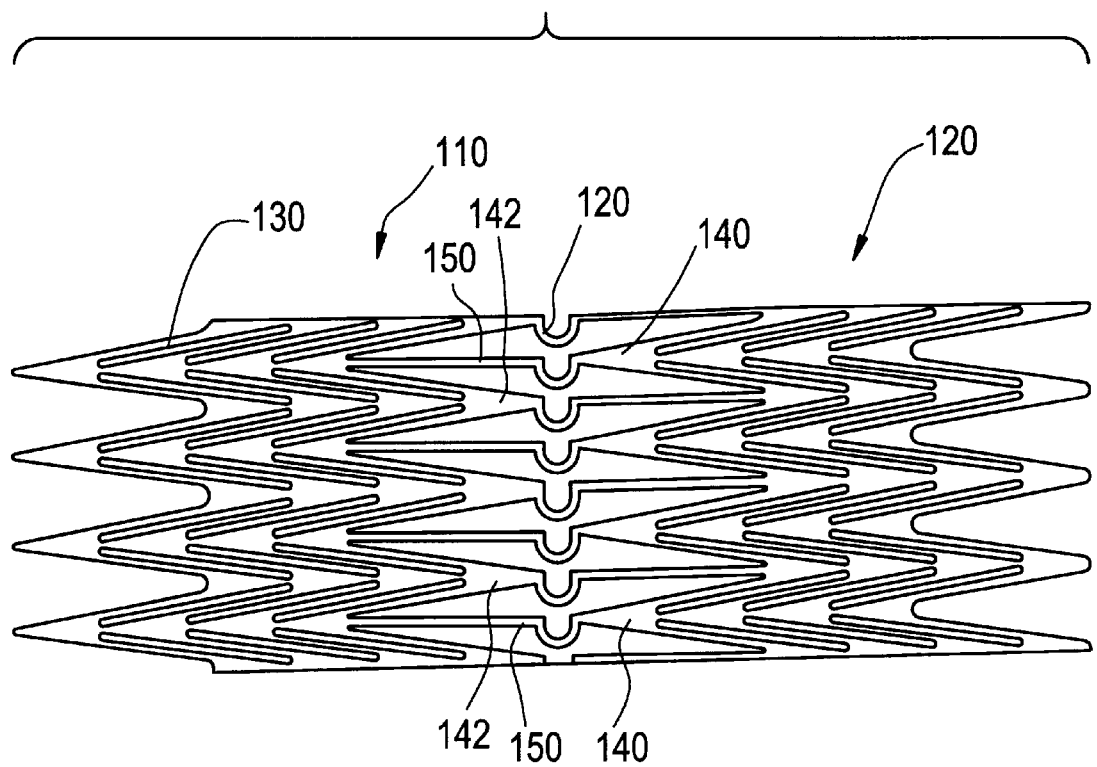
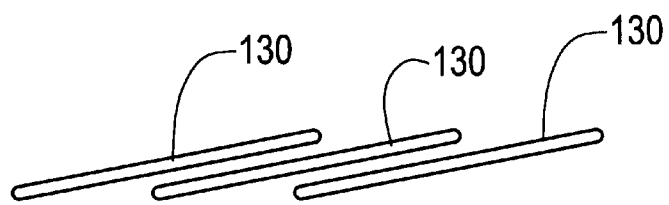

COATED INTRALUMINAL GRAFT

The present invention claims the benefit of the filing date of United States Provisional Patent Application Serial No. 60/094,250 filed Jul. 27,1998 entitled "Coated Graft." The present invention is also a continuation-in-part of co-pending U.S. patent application Ser. No. 09/273,736 filed Mar. 22, 1999, now pending entitled "Improved Expandable Graft," which in turn claims the benefit of the filing date of United States Provisional Patent Application Serial No. 60/081,824 filed Apr. 15, 1998.

This invention relates to an improved intraluminal graft for use within a body passageway, duct, blood vessel or other cavity and, more particularly, expandable intraluminal grafts for use within a body passageway, duct, blood vessel or other cavity and, more particularly, expandable intraluminal grafts which are particularly useful for repairing blood vessels narrowed or occluded by disease and which graft is at least partially coated with a drug or compound that inhibits biological components capable of causing adverse clinical affects. Here after the terms "graft" and "stent" are interchangeable.

DESCRIPTION OF THE PRIOR ART

Heart disease is still one of the most prevalent medical ailments in the world. Intraluminal endovascular grafting, a type of angioplasty procedure, has been demonstrated by experimentation to present a possible alternative to conventional vascular surgery and is used to treat heart disease. Intraluminal endovascular grafting involves a tubular prosthetic graft and its delivery within the vascular system. Advantages of this method over conventional vascular surgery include obviating the need for surgically exposing, incising, removing, replacing, or bypassing the defective blood vessel. Over 20 million angioplasty or related procedures involving occluded vasculature have been performed worldwide.

Several years ago, a product called a stent was introduced for use in angioplasty procedures. A stent is an expandable metal tubular device that is mounted over an angioplasty balloon and deployed at the site of coronary narrowing. The balloon is inflated to expand the stent so as to physically open and return patency to the body passageway, duct or blood vessel. The balloon is then deflated and the stent is permanently disposed to retain the passageway, duct or blood vessel open. One particular type of stent is disclosed in U.S. Pat. No. 4,733,665. This stent overcame the problem associated with controlled expansion of the stent. In the prior art, there was no control over the final, expanded configuration of the stent. For instance, the expansion of a particular coiled spring-type stent was predetermined by the method of manufacturing, material and delivery system. In the case of self-expanding intraluminal grafts, or prostheses, formed of a heat sensitive material which expands upon exposure to core body temperature, the amount of expansion was predetermined by the heat expansion properties of the particular alloy utilized in the manufacture of the intraluminal graft. Thus, once the foregoing types of intraluminal grafts were expanded at the desired location within a body passageway, such as within an artery or vein, the expanded size of the graft cannot be increased. If the diameter of the desired narrow lumened body passageway had not been determined correctly, the graft might not expand enough to contact the interior surface of the body passageway, so as to be secured thereto. The stent disclosed in the '665 patent overcame the problems associated with these past stent designs.

The stent based upon the '665 patent is currently being used in angioplasty procedures. However, this stent has several shortcomings which contribute to procedural failure rates. The currently used stents are not readily visible under fluoroscopic guidance procedurally. Stent placement is hindered as a result of poor visibility. These stents also shorten longitudinally after radial expansion, which is not desirable for their intended use.

These problems with current stent technology are overcome in my co-pending U.S. patent application Ser. No. 09/273,736 filed Mar. 22, 1999 entitled "Improved Expandable Graft," which is incorporated herein by reference. My improved stent improves the visibility under fluoroscopy in vivo and retains its longitudinal dimensions from its original pre-expanded configuration to the expanded state.

Several problems can develop after the stent is inserted into a passageway. One problem is known as in-stent restenosis wherein the passageway, which has been previously treated with a stent, renarrows or closes within the stented segment. The renarrowing or closure of the passageway can be caused by a structural failure of the stent due to contractive forces by the passageway on the stent and/or by the passageway growing into the openings in the stent. Other problems can include vascular narrowing and restenosis. Vascular narrowing is defined as a vascular segment that has not been previously treated by any interventional means and eventually closes preventing blood flow. Restenosis is the renarrowing of a previously treated vascular segment not involving a stent. Both of these problems are the result of a passageway that was not treated with an invasive angioplasty, narrowing or closing. Both of the problems result from the insertion of a stent in one portion of the passageway causing vascular narrowing or restenosis in another part of the passageway.

Vascular narrowing, restenosis and in-stent restenosis are caused by biological factors causing the premature closing of vessels. One such agent is platelet derived growth factors, referred to as PDGF. PDGF is an intercellular messenger capable of stimulating proliferation of smooth muscle cells. Smooth muscle cells migrate within the artery and cause a restenotic reaction.

In view of the problems which can result from the insertion of a stent into a passageway, there is a need and demand for a stent that reduces the occurrence of in-stent restenosis and can also reduce the occurrence of vascular narrowing and restenosis in untreated portions of a passageway.

SUMMARY OF THE INVENTION

This invention pertains to an improved intraluminal graft that is designed to meet the present-day needs and demands relating to intraluminal grafts. The present invention includes a geometrically shaped member, having first and second ends and a wall surface disposed between the first and second ends. The wall surface is preferably formed by a plurality of intersecting elongated members, and at least some of the elongated members preferably intersect with one another at a point intermediate to the first and second ends of the tubular shaped member. The tubular shaped member has a first diameter which permits intraluminal delivery of the tubular shaped member into a body passageway having a lumen and a second, expanded diameter. The expansion of the tubular shaped member can be accomplished in a variety of manners. Preferably, the tubular shaped member is expanded to its second diameter by a radially, outwardly extending force that is applied at least partially from the interior of the tubular shaped member. The second diameter of the tubular shaped member is variable and dependent upon the amount of radially outward force applied to the tubular shaped member. Preferably, the tubular shaped member is expandable, to allow expansion of the lumen of the body passageway while retaining its, the tubular shaped member's, original length. At least a portion of the graft is preferably coated with a substance which inhibits the occurrence of in-stent restenosis, vascular narrowing and/or restenosis.

Another feature of the present invention is that the plurality of elongated members include a plurality of wires, and the wires may be fixedly secured to one another where the wires intersect with one another. In one specific embodiment, the tubular member is at least partially made of a wire mesh tube. The wire mesh tube may be utilized as the intraluminal graft. The wire mesh tube can be radially expanded to a second diameter within the body passageway; the second, expanded diameter being variable and determined by the desired expanded internal diameter of the body passageway, duct, blood vessel, etc., whereby the expanded wire mesh tube will not migrate from the desired location within the body passageway, duct, blood vessel, etc., and the expansion of the intraluminal graft does not cause a rupture of the body passageway, duct, blood vessel, etc.

Yet another feature of the present invention is that the plurality of elongated members includes a plurality of thin bars which are fixedly secured to one another where the bars intersect with one another.

Still yet another feature of the present invention is that the elongated members form at least one parallelogram which upon expansion, retains the original longitudinal length of the graft.

Another feature of the present invention is that the graft includes at least one set of slots arranged with respect to one another to maintain the original longitudinal length of the graft when the graft is expanded.

Yet another feature of the present invention is that the graft is at least partially formed by an etching process and/or by laser cutting.

Still another feature of the present invention is that the intraluminal graft member has a biologically inert coating on at least a portion of its wall surface. The coating can be used to reduce infection, irritation and/or rejection of the intraluminal graft.

Still yet another feature of the present invention is that the intraluminal graft, upon expansion, substantially maintains its original longitudinal length.

Another feature of the present invention is that the intraluminal graft includes at least two tubular members that are connected together by at least one connector that allows transverse bending and flexibility invariant to the plane of bending. Preferably, the connector is a "U" shaped connector.

Yet another feature of the present invention is that the tubular shaped member is made of and/or includes a material that is more visible under fluoroscopy in vivo than currently available stents. The tubular member preferably includes a special material such as gold to enhance the visibility of the tubular member in a body passageway, duct, blood vessel, etc.

Still yet another feature of the present invention is that the material to make the tubular member includes a second material that is visible under fluoroscopy. Preferably, the second material is secured to at least a portion of the outer surface of the base material of the tubular member such as by adhering, mounting, welding, brazing or the like, to enhance the visibility of the tubular member under fluoroscopy. Preferably, the second material is secured to the other surface of the base material at a location so as to substantially only come in contact with the inner luminal surface of the vessel, and not any blood borne components that could accelerate stent failure rates. In one specific embodiment, the second material is at least partially located at at least one end, and preferably both ends, of the tubular member. This positioning of the material on the stent helps to identify the location of the ends of the stent, thus enhancing the critical placement of the stent so as to reduce the failure rate. In another specific embodiment, the second material is at least partially located on the outer surface of the tubular member at the connecting flexible joints of the tubular member. This location of the second material also enhances the critical placement of the stent around areas of high tortuosity so as to reduce the failure rate.

Still another feature of the present invention is that the tubular member is at least partially treated with Gamma or Beta radiation to reduce the vascular narrowing of the stented section. The radioactive treatment helps to inactivate the cell migration and properties thereof within about a 3 mm depth of the arterial wall.

Still yet another feature of the present invention is that the intraluninal graft can be inserted and expanded by standard procedures. Therefore, the intraluminal graft can be inserted into a body passageway, duct, blood vessel, etc. until it is disposed at the desired location within the body passageway. The intraluminal graft is then expanded outwardly into contact with the body passageway until the lumen of the body passageway at the desired location, luminal narrowing, has been expanded, whereby the intraluminal graft prevents the body passageway from collapsing.

A further feature of the present invention is that the graft is at least partially coated with a substance that inhibits and/or reduces restenosis, vascular narrowing and/or in-stent restenosis.

Another feature of the present invention is that a substance is at least partially coated onto the graft to inhibit PDGF activity in the passageway. After a stent is inserted into a passageway, the stent may induce some irritation in the passageway. The biological factor, PDGF, is turned on due to such irritation and activates the components of clotting. These components can cause clotting in the stent area or in adjacent areas. This clotting can cause the passageway to narrow or ultimately close. The substance coated on the stent is formulated to deactivate and/or inhibit the activity of the PDGF, thereby reducing the occurrence of in-stent restenosis, vascular narrowing and/or restenosis.

Yet another feature of the present invention is that the PDGF inhibitor is preferably triazolopyrimidime (Trapidil). A damaged endothelium exposes the connective tissue to platelet aggregation and to local release of PDGF. Numerous animal models have shown that platelet adhesion to the vascular wall of this damaged endothelium soon triggers the proliferation and migration of smooth muscle cells. If platelets are a source of PDGF, it has now been demonstrated that endothelial cells, macrophages and smooth muscle cells are also a source of PDGF following vascular trauma. The influence of Trapidil on platelet aggregation is linked to inhibition of the synthesis of thromboxane A2 and the partial blocking of thromboxane A2 receptors. Trapidil is able to normalize an incorrect balance between thromboxane A2 and prostacycline. Thromboxane A2 is a powerful inducer of platelet aggregation. It is also responsible for the contraction of smooth muscles of vessels and stimulates the proliferation of the arterial intimal cells. Prostacyclin inhibits platelet aggregation and vasodilator properties. Trapidil also has antithrombotic properties. It can significantly reduce thrombosis induced by creation of an arteriovenous conduit, as compared to aspirin and dipyridamole, which only had a modest affect. Trapidil has other desirable properties such as vasodilation, a decrease in angina and an increase in HDL levels in patients with ischemic heart disease. Trapidil, at present, represents the most fully documented agent demonstrating a pharmacological and clinical effect in inhibition of restenosis. Prior substances have been coated onto stents to address one or more problems associated with the use of stents. These substances include heparin, colchicine and dexamethazone, among others. These substances are used to inactivate platelets, stop cell division and prevent cell adhesion. The problems associated with the use of these substances have varied effects. Heparin is not potent enough to extend a clinical affect. Colchicine has been shown to kill the cells in the surrounding area and actually propagate the problem. And dexamethazone has not provided the desired restenosis prevention. However, as can be appreciated, aspirin, colchicine, dexamethazone dipyridamocs, heparin and/or derivatives thereof can be substituted for, or used in combination, with Trapidil on the stent. Trapidil has a affinity to exert clinical effects starting in the second hour of treatment. This inhibition of platelet aggregation is reflected in a significant increases in collagen and ADP. The platelet inhibition in the first day of treatment with Trapidil continues through the thirtieth day. The philosophy of a multifactoral approach, including but not limited to the increasing success of angioplasty and stent associated with a considerable reduction in complications, has been the reason behind the use of this technique in a large scale in the treatment of patients with coronary heart disease. Restenosis is the most important limitation to the long term benefits of angioplasty and a stent combination. A pharmacological approach aiming to intervene in the mechanism of restenosis will be needed to supplement the mechanical approach of the revascularization procedure. Various approaches have been proposed for the prevention of restenosis. To use a novel drug such as Trapidil delivered as a coating on a stent locally to the affected area hereby corresponds to this approach.

Still yet another feature of this invention corresponds to the local delivery of the substance to inhibit and/or prevent restenosis, vascular narrowing and/or in-stent restenosis, such as Trapidil, through an angioplasty balloon with the physical capability to transfer solute of the substance through the balloon membrane to the affected sight. This delivery can be in the form of a stream, a slow oozing delivery or a bolus injection. The delivery can be made through magnetic, electrical or physical means. The delivery is accomplished through a separate lumen capable of channeling the solute of the substance to the affected area. This delivery through a balloon also delivers the substance to the sight of restenosis, vascular narrowing and/or in-stent restenosis.

Still yet another feature of the present invention is that the substance to inhibit and/or reduce restenosis, vascular narrowing and/or in-stent restenosis may be partially coated on specific regions of the stent or may be totally coated on the stent. The thickness of the coating is not as important as the concentration of the substance needed to acquire the desired affect.

Still another feature of the present invention is the substance to inhibit and/or reduce restenosis, vascular narrowing and/or in-stent restenosis is coated onto the stent by the use of an intermediate compound. Preferably, the compound is a synthetic or biocapatable material that does not adversely affect the substance or cause problems or adverse reactions in the passageway.

In summary, the present invention includes a radially expandable, tubular shaped prosthesis having first and second ends and a wall surface disposed between the first and second ends, the wall surface being formed by a plurality of intersecting elongated members and is at least partially coated with a substance that reduces stent failure and/or narrowing or closure of a non-treated portion of the passageway.

BRIEF DESCRIPTION OF THE DRAWINGS

Reference may now be made to the drawings, which illustrate various embodiments that the invention may take in physical form and in certain parts and arrangements of parts wherein:

FIG. 2 is an enlarged perspective view of the graft of FIG. 1 in a non-tubular state;

FIG. 3 is a sectional view of the graft of FIG. 2 showing a connector used to connect the ends of two tubular sections of the graft;

FIG. 7 is a sectional view of the graft of FIG. 5 showing the location and angular orientation of the opening in the graft;

DETAILED DESCRIPTION OF THE INVENTION

Figure 1:
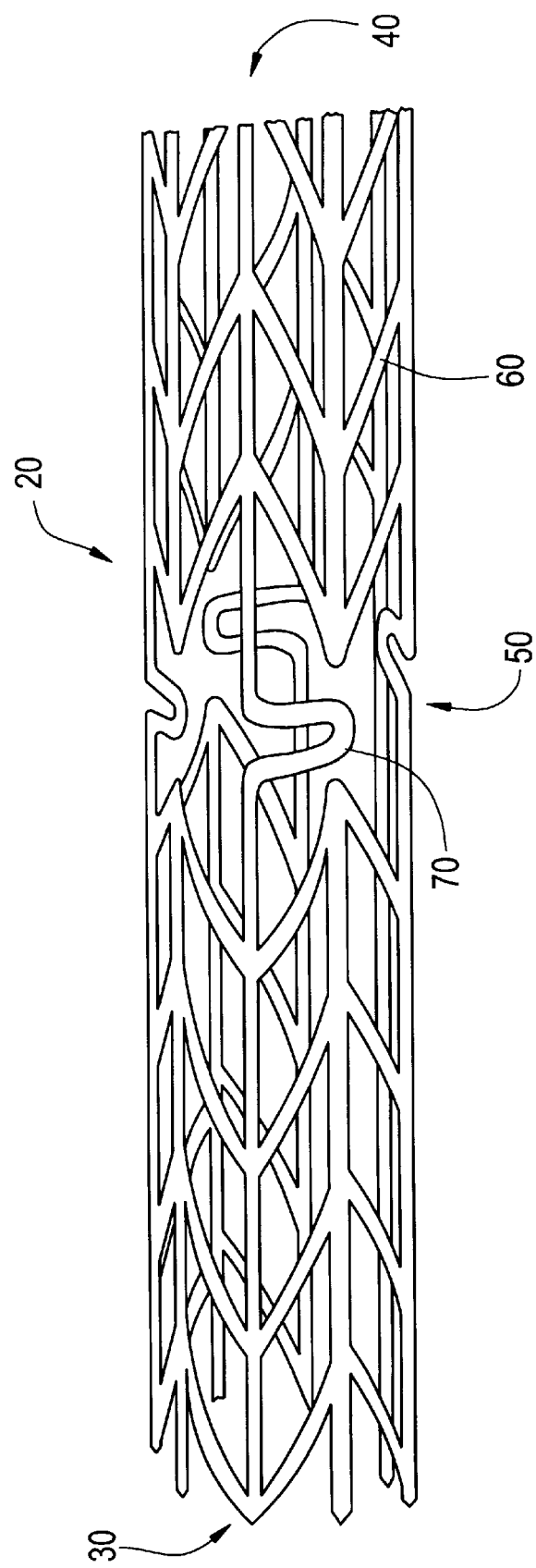
FIG. 1 is a perspective view of an intraluminal graft which permits delivery of the graft, or prosthesis, into a body passageway.
Figure 4:
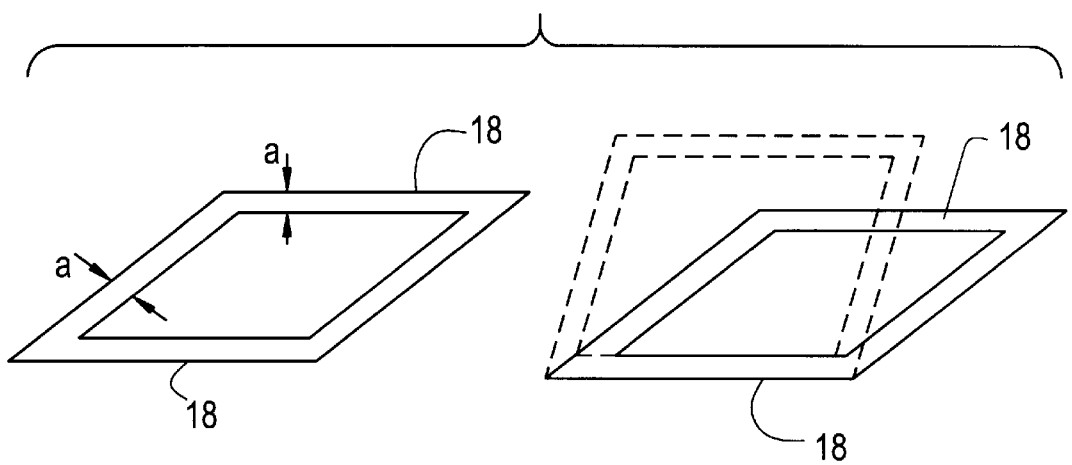
FIG. 4 is an enlarged sectional view of the graft of FIG. 2 showing the parallelogram structure of the graft before and after expansion.

Referring now to the drawings wherein the showing is for the purpose of illustrating preferred embodiments of the invention only and not for the purpose of limiting the same, the FIGS. 1–9 disclose an intraluminal graft, such as an expandable prosthesis, for a body passageway. It should be understood that the terms "expandable intraluminal graft", "expandable prosthesis" and "stent" are interchangeably used to some extent in describing the present invention. The apparatus and structures of the present invention may be utilized not only in connection with an expandable intraluminal graft for expanding partially occluded segments of a blood vessel, or body passageway, but also for additional uses. For example, but not limited to, the expandable prostheses may be used for such purposes as 1) a supportive graft placement within a blocked vasculature opened by transluminal recanalization, which are likely to collapse in the absence of an internal support; 2) forming a catheter passage through mediastinal and/or other veins occluded by inoperable cancers; 3) reinforcement of catheter created intrahepatic communications between portal and/or hepatic veins in patients suffering from portal hypertension; 4) supportive graft placement of narrowing of the esophagus, the intestine, the ureter and/or the urethra; 5) and supportive graft reinforcement of reopened and previously obstructed bile ducts. Accordingly, use of the term "prosthesis" encompasses the foregoing usages within various types of body passageways, and the use of the term "intraluminal graft" encompasses use for expanding the lumen of a body passageway. Further, in this regard, the term "body passageway" encompasses any duct within the human body, such as those previously described, as well as any vein, artery, and/or blood vessel within the human vascular system.

The expandable intraluminal graft as shown in the FIGS. 1, 2, 3 and 4 generally comprises a tubular shaped member 20 having a first end 30 and a second end 40 and a wall surface 50 disposed between the first and second ends. Preferably, the wall surface is formed by a plurality of intersecting elongated members 60 with at least some of the elongated members intersecting with one another intermediate the first and second ends of the tubular shaped member. The tubular shaped member has a first diameter which permits intraluminal delivery of the tubular shaped member into a body passageway having a lumen. FIG. 1 shows a perspective view of a section of the tubular shaped member 20 which has a second, expanded diameter, which second diameter is variable in size.

Elongated members 60, which form the wall surface of the tubular shaped member may be any suitable material which is compatible with the human body and the bodily fluids with which the graft, or prosthesis, may come into contact. Preferably, the elongated members are made of a material, include and/or are coated with a material that is readily visible in vivo under fluoroscopic view. The elongated members also are made of a material which has the requisite strength and elasticity characteristics to permit the tubular shaped member to be expanded from its original tubular form to its expanded tubular form, and to further to permit the tubular shaped member to retain its expanded configuration with the enlarged diameter. Suitable materials for the fabrication of the tubular shaped structure of include tantalum, stainless steel, titanium or any suitable plastic material having the requisite characteristics previously described. Preferably, the tubular shaped structure is made of stainless steel.

Elongated members 60 are generally small diameter wires or bars that have a maximum cross-sectional length or diameter of up to about 0.02 inches, and preferably about 0.0005 to 0.008 inches. It should, of course, be understood that each elongated member can have a variety of different cross-sectional configurations, along part or the complete length of each member. Such configurations include circular, oval, diamond, triangular, square, rectangular, hexagonal, etc.

A plurality of elongated members can be connected together to form the tubular member. To provide flexibility to the tubular member, the elongated members are connected together by a connector. One such connector is a "U" shaped member 70 where the elongated members 60 join with one another as shown in FIGS. 1–3.

The elongated members can be formed by a variety of processes. Preferably, the elongated members are formed by etching a single tubular piece of material so that each individual intersections of the elongated members need not be welded. For example, a tubular shaped member is initially formed from a thin-walled metal tube, and the openings between the intersecting bars are formed by a conventional etching process, such as electromechanical or laser etching, whereby the resultant structure is a tubular shaped member having a plurality of intersecting elongated members as shown in FIGS. 1 and 2. This technique enhances the structural integrity of the tubular structure and reduces the number of rough surfaces at the intersection points.

One particular design of the pattern of the tubular member is shown in FIGS. 1 and 2. The openings between the intersecting bars are preferably generally parallelogram in shape. The openings are positioned to form a pattern as shown in the FIG. 4. As can be appreciated, this parallelogram pattern allows the tubular shaped members to be expanded without the members having a reduction in length in the longitudinal direction. Since a parallelogram is a four sided figure with opposite sides parallel, the longitudinal axis of structure of member 60 will remain the same as the sides are elongated and as the angle of the parallelogram changes during expansion. Preferably, the surface of the tubular member is formed by a plurality of parallelograms.

As shown in FIG. 1, the arrangement for connecting two tubular members 60 together is by at least one "U" shaped member 70 to increase the flexibility of the graft. The connector is shown to be a "U" shaped member 70 that connects two ends of the tubular members 60 together. As shown in FIGS. 1–3, a plurality of "U" shaped members 70 are used to connect a set of two adjacently positioned ends of one tubular member to a corresponding set of adjacently positioned ends in the other tubular member. This configuration allows at least two tubular members that are connected together by at least one set of circularly distributed "U" shaped connector to transverse bend and improve flexibility invariant to the plane of bending. As can be appreciated, other shaped connectors which include an arcuate portion can be used.

Referring now to FIGS. 2 and 3, the size of the "U" shaped connector is a function of the size and spacing of the elongated members. The length of the "U" shaped member is preferably about the sum of twice the thickness of the wire or bars of the elongated members plus the height of the parallelogram in the non-expanded shape (2a+b). The spacing of a non-connected end of an elongated member from the "U" shaped member when the tubular shaped member 20 is in a nonexpanded position is about equal to the thickness of the elongated member. The spacing and configuration enables the desired flexibility of the tubular member and proper expansion of the tubular member.

Figure 8:
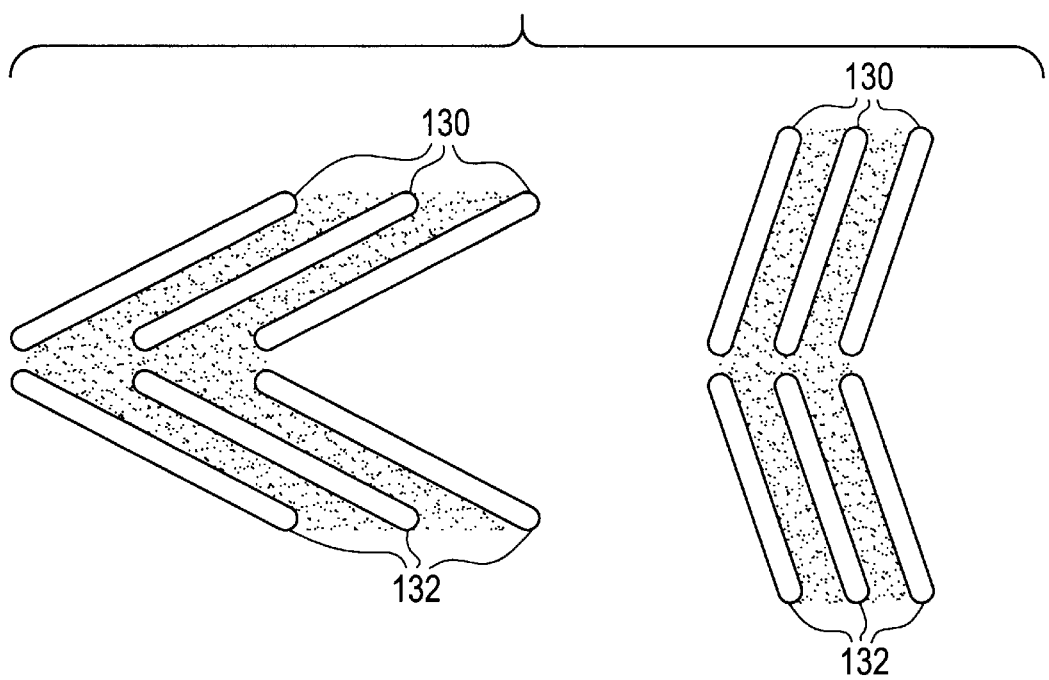
FIG. 8 is an enlarged sectional view of the graft of FIG. 5 showing a part of the structure of the graft before and after expansion.
Figure 5:
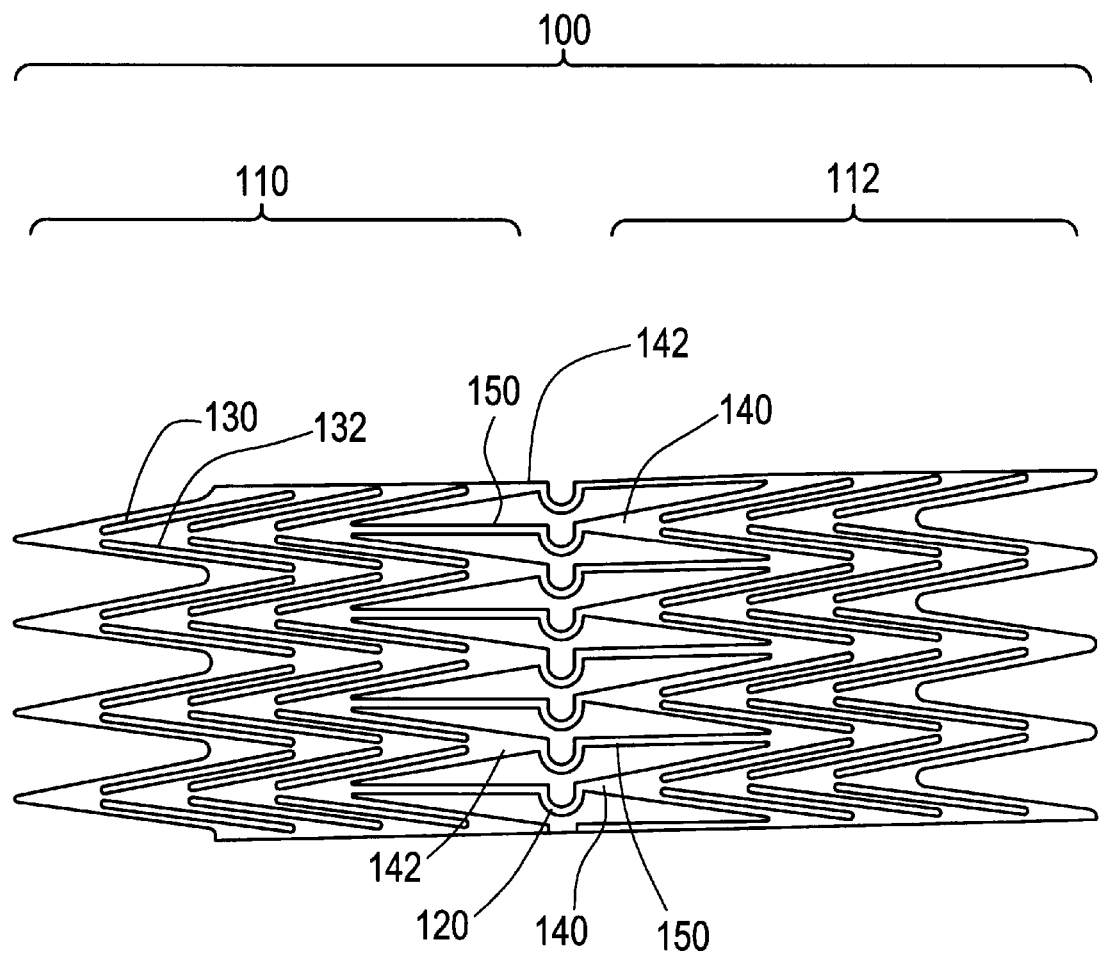
FIG. 5 is a perspective view of an additional embodiment of the present invention.
Figure 6:
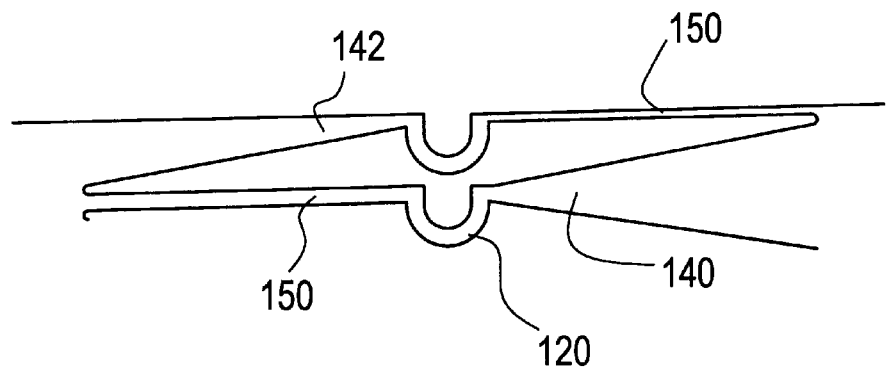
FIG. 6 is an enlarged sectional view of the graft of FIG. 5 showing a connection used to connect the ends of two sections of the graft together.

Referring now to FIGS. 5, 6, 7 and 8, a second embodiment of the present invention is illustrated. As shown in FIG. 5, a graft 100 includes two sections 110, 112. However, graft 100 may include more than two sections. The two sections 110, 112 are connected together by a connector 120. Preferably, connector 120 is arcuate in shape and more preferably is "U" shaped. As shown in FIG. 5, sections 110, 112 are substantially symmetrical to one another and preferably have substantially identical dimensions. Each section includes a plurality of slots 130, 132. Slots 130, 132 are preferably equal in length and width. Each series of slots 130 are arranged substantially parallel to one another. Each series of slots 132 are also arranged substantially parallel to one another. Slots 130 and 132 are positioned relative to one another to form an angle between 0–90° when the graft is in the unexpanded position as shown in FIG. 5. The slot arrangement between ends 140 and 142 of graft 100 allow the graft, when expanded radially, to retain its original pre-expanded length. The configuration of the slots 130, 132 in the pre-expanded and post-expanded position is shown in FIG. 8. The slots can be formed in a variety of manners. Preferably, the slots are formed by laser cutting. The formation of slots 130, 132 by use of a laser is shown in FIG. 7. The configuration of connectors 120 is shown in FIG. 6. As shown in FIGS. 5 and 6, connectors 120 are secured to an extension bar 150 and to end 140 of the second section 112 or to end 142 of the first section 110. Extension bar 150 alternates connection between end 142 of the first section 110 and end 140 of the second section 112.

Figure 9:
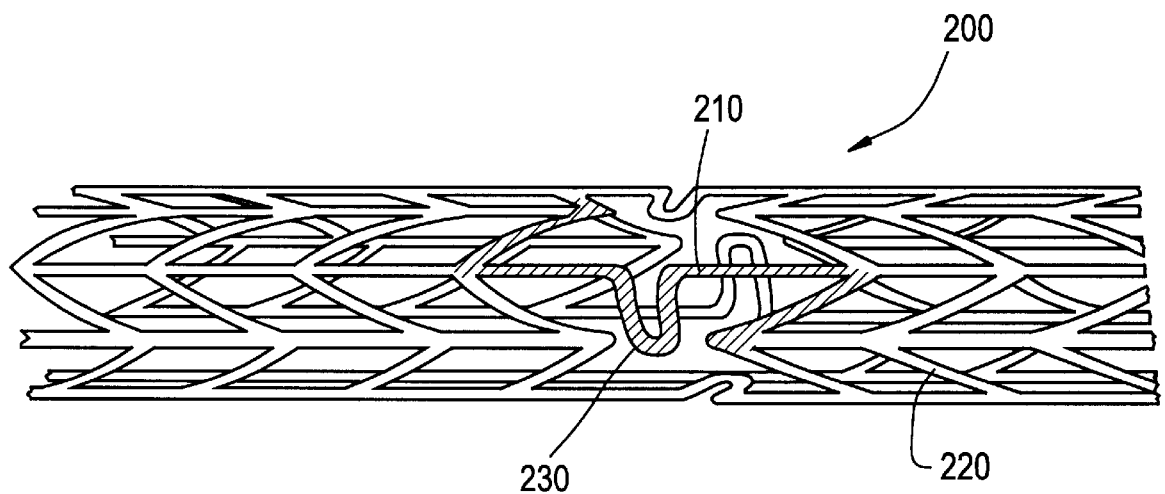
FIG. 9 is a perspective view of an intraluminal graft of FIG. 1 showing a coating of a substance on the graft.

Referring now to FIG. 9, a tubular member 200 is shown to include a compound 210 on the elongated members 220 and connector 230 of the tubular member. Compound 210 is a substance that inhibits and/or prevents restnosis, vascular narrowing and/or in-stent restenosis. One preferable compound is a PDGF inhibitor such as Trapidil.

As can be appreciated, the amount of PDGF inhibitor delivered to a certain region of a passageway can be controlled by varying the coating thickness, drug concentration of the PDGF inhibitor and/or the amount of surface area of the tubular member 200 is coated with the PDGF inhibitor. As can also be appreciated, the PDGF inhibitor can be combined with or at least partially coated with a substance that affects the rate to which the PDGF inhibitor is released from the surface of the stent. A bonding compound can be used on conjunction with compound 210 to assist in binding compound 210 to tubular member 200. In addition, or alternatively, the bonding compound can be used to control the release of compound 210 into the body passageways. In one particular application, the bonding compound is biodegradable and dissolves over the course of time. The bonding agent is coated at one or more thicknesses over compound 210 to delay delivery of compound 210 into a body passageway.

Figure 10:
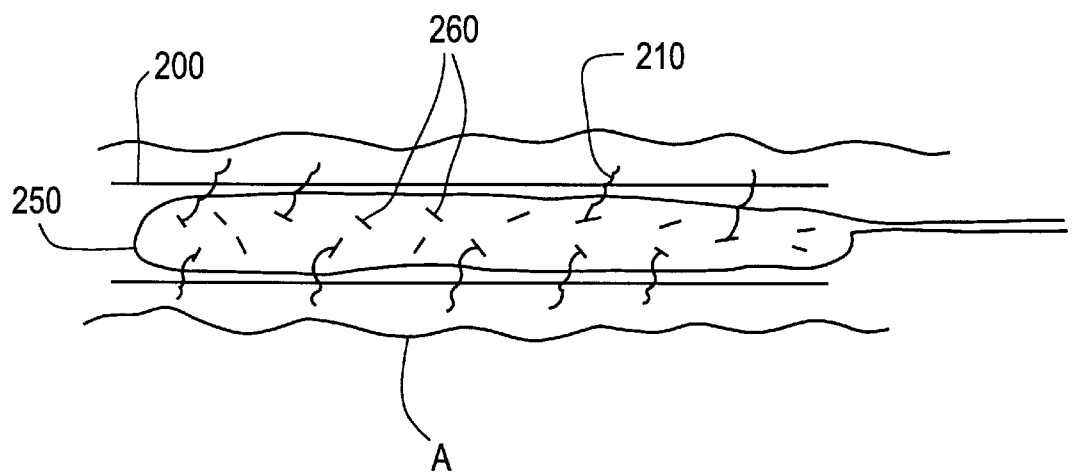
FIG. 10 is a perspective view of an angioplasty balloon delivering fluid materials to a local site.

Referring now to FIG. 10, compound 210 is delivered into a body passageway A via balloon 250. Balloon 250 includes one or more slots 260 to allow delivery of compound 210 into body passageway A. Balloon 250 can be used to both deliver compound 210 and expand tubular member 200, or be used in conjunction with another balloon or tubular member expanding device. Due to the properties of the PDGF inhibitor, local delivery of the inhibitor by a stent is highly advantageous.

The present invention has been described with reference to a number of different embodiments. It is to be understood that the invention is not limited to the exact details of construction, operation, exact materials or embodiment shown and described, as obvious modifications and equivalents will be apparent to one skilled in the art. It is believed that many modifications and alterations to the embodiments disclosed will readily suggest themselves to those skilled in the art upon reading and understanding the detailed description of the invention. It is intended to include all such modifications and alterations insofar as they come within the scope of the present invention.

What is claimed is:

1. An intraluminal graft for use within in a body cavity including a geometrically shaped member and a biological agent, said geometrically shaped member having first and second ends and a wall surface disposed between the first and second ends, the wall surface being formed by a plurality of intersecting elongated members, at least some of the elongated members intersecting with one another intermediate the first and second ends of the geometrically shaped member, said geometrically shaped member having a first diameter which permits intraluminal delivery of the geometrically shaped member into a body cavity, and a second expanded diameter, said biological agent being at least partially coated on the surface of said geometrically shaped member, said biological agent including a compound to inhibit or reduce a biological condition selected from the group consisting of restenosis, vascular narrowing, in-stent restenosis and combinations thereof, at least a portion of said biological agent releasably coated on a surface of said graft.

2. The expandable intraluminal graft as defined in claim 1, wherein said biological agent includes a platelet inhibitor.

3. The expandable intraluminal graft as defined in claim 2, wherein said platelet inhibitor includes Trapidil.

4. The expandable intraluminal graft as defined in claim 3, wherein said body cavity is selected from the group consisting of a body passageway, body duct or a body blood vessel.

5. The expandable intraluminal graft as defined in claim 4, wherein said second diameter is variable.

6. The expandable intraluminal graft of claim 5, wherein the plurality of elongated members are a plurality of wires, and the wires are fixedly secured to one another where the wires intersect with one another.

7. The expandable intraluminal graft of claim 5, wherein the plurality of elongated members are a plurality of thin bars which are fixedly secured to one another where the bars intersect with one another.

8. The expandable intraluminal graft of claim 5, wherein said geometrically shaped member includes a plurality of openings.

9. The expandable intraluminal graft of claim 5, wherein said graft includes two geometrically shaped members and at least one connector connected between the two geometrically shaped members, said connector allowing transverse bending flexibility of said graft.

10. The expandable intraluminal graft of claim 5, wherein said geometrically shaped member includes material to make the geometrically shaped member visible under fluoroscopy.

11. The expandable intraluminal graft as defined in claim 10, wherein said geometrically shaped member is at least partially coated with a material that is visible under fluoroscopy.

12. The expandable intraluminal graft as defined in claim 11, wherein said material is coated on at least one end of said geometrically shaped member.

13. The expandable intraluminal graft of claim 12, wherein said intersecting elongated members are formed by etching and/or laser cutting.

14. The expandable intraluminal graft of claim 13, including a mounting substance to be at least partially coated on said graft, said mounting substance at least partially securing said biological agent to said graft.

15. The expandable intraluminal graft as defined in claim 14, wherein said mounting substance at least partially delays delivery of said biological agent into said body cavity.

16. The expandable intraluminal graft as defined in claim 15, including balloon, said balloon including at least one opening to allow delivery of said biological substance from an interior of said balloon to said body cavity.

17. The expandable intraluminal graft as defined in claim 16, wherein said biological substance includes said biological agent.

18. The expandable intraluminal graft of claim 17, wherein said geometrically shaped member is treated with Gamma or Beta radiation to reduce the vascular narrowing of at least a portion of said body cavity.

19. The expandable intraluminal graft of claim 18, wherein said geometrically shaped member is substantially tubular.

20. The expandable intraluminal graft as defined in claim 5, wherein said geometrically shaped member is at least partially coated with a material that is visible under fluoroscopy.

21. The expandable intraluminal graft as defined in claim 2, wherein said second diameter is variable.

22. The expandable intraluminal graft of claim 2, including a mounting substance to be at least partially coated on said graft, said mounting substance at least partially securing said biological agent to said graft.

23. The expandable intraluminal graft as defined in claim 22, wherein said mounting substance at least partially delays delivery of said biological agent into said body cavity.

24. The expandable intraluminal graft as defined in claim 23, including balloon, said balloon including at least one opening to allow delivery of said biological substance from an interior of said balloon to said body cavity.

25. The expandable intraluminal graft as defined in claim 24, wherein said biological substance includes said biological agent.

26. The expandable intraluminal graft as defined in claim 22, including balloon, said balloon including at least one opening to allow delivery of said biological substance from an interior of said balloon to said body cavity.

27. The expandable intraluminal graft as defined in claim 26, wherein said biological substance includes said biological agent.

28. The expandable intraluminal graft as defined in claim 2, including balloon, said balloon including at least one opening to allow delivery of said biological substance from an interior of said balloon to said body cavity.

29. The expandable intraluminal graft as defined in claim 28, wherein said biological substance includes said biological agent.

30. The expandable intraluminal graft as defined in claim 1, wherein said body cavity is selected from the group consisting of a body passageway, body duct or a body blood vessel.

31. The expandable intraluminal graft as defined in claim 1, wherein said second diameter is variable.

32. The expandable intraluminal graft of claim 1, wherein the plurality of elongated members are a plurality of wires, and the wires are fixedly secured to one another where the wires intersect with one another.

33. The expandable intraluminal graft of claim 1, wherein the plurality of elongated members are a plurality of thin bars which are fixedly secured to one another where the bars intersect with one another.

34. The expandable intraluminal graft of claim 1, wherein said geometrically shaped member includes a plurality of openings.

35. The expandable intraluminal graft of claim 1, wherein said graft includes two geometrically shaped members and at least one connector connected between the two geometrically shaped members, said connector allowing transverse bending flexibility of said graft.

36. The expandable intraluminal graft of claim 1, wherein said geometrically shaped member includes material to make the geometrically shaped member visible under fluoroscopy.

37. The expandable intraluminal graft as defined in claim 1, wherein said geometrically shaped member is at least partially coated with a material that is visible under fluoroscopy.

38. The expandable intraluminal graft as defined in claim 37, wherein said material is coated on at least one end of said geometrically shaped member.

39. The expandable intraluminal graft of claim 1, wherein said intersecting elongated members are formed by etching and/or laser cutting.

40. The expandable intraluminal graft of claim 1, including a mounting substance to be at least partially coated on said graft, said mounting substance at least partially securing said biological agent to said graft.

41. The expandable intraluminal graft as defined in claim 40, wherein said mounting substance at least partially delays delivery of said biological agent into said body cavity.

42. The expandable intraluminal graft as defined in claim 1, including balloon, said balloon including at least one opening to allow delivery of said biological substance from an interior of said balloon to said body cavity.

43. The expandable intraluminal graft as defined in claim 42, wherein said biological substance includes said biological agent.

44. The expandable intraluminal graft of claim 1, wherein said geometrically shaped member is treated with Gamma or Beta radiation to reduce the vascular narrowing of at least a portion of said body cavity.

45. The expandable intraluminal graft of claim 1, wherein said geometrically shaped member is substantially tubular.

* * * * *